US00PP30489P3

(12) United States Plant Patent
Danziger

(10) Patent No.: US PP30,489 P3
(45) Date of Patent: May 7, 2019

(54) ***SUTERA* PLANT NAMED 'DCOPGRAZUR'**

(50) Latin Name: *Sutera cordata*
Varietal Denomination: DCOPGRAZUR

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 57 days.

(21) Appl. No.: 15/731,181

(22) Filed: Apr. 28, 2017

(65) Prior Publication Data

US 2018/0317365 P1 Nov. 1, 2018

(51) Int. Cl.
*A01H 5/02* (2018.01)
*A01H 6/00* (2018.01)

(52) U.S. Cl.
USPC ..... Plt./485
CPC ..... *A01H 6/00* (2018.05); *A01H 5/02* (2013.01)

(58) Field of Classification Search
USPC ..... Plt./485
CPC ... A01H 5/02; A01H 5/00; A01H 1/02; A01H 6/00
See application file for complete search history.

(56) References Cited

PUBLICATIONS

Danziger Great Azure Scopia Series: Bacopa—Annual Flowers, retrieved on Aug. 15, 2018, retrieved from the Internet at https://danzigeronline.com/variety/scopia-great-azure/, 5 pp. (Year: 2018).*
Gro 'n Sell Quality Starter Plants 2016-2017 Catalog, retrieved on Aug. 15, 2018, retrieved from the Internet at http://www.messickco.com/uploads/GroNSellCatalog-2016-2017.pdf, 2 cover pages, 1-2, 58, 102-103. (Year: 2016).*

* cited by examiner

*Primary Examiner* — June Hwu
(74) *Attorney, Agent, or Firm* — Cassandra Bright

(57) ABSTRACT

A new and distinct *Sutera* cultivar named 'DCOPGRAZUR' is disclosed, characterized by early and abundant flowering, extra-large violet-blue single flowers with a violet center halo, medium plant vigor and a semi-trailing growth habit. The new variety is a *Sutera*, normally produced as an outdoor garden or container plant.

2 Drawing Sheets

Figure 1:
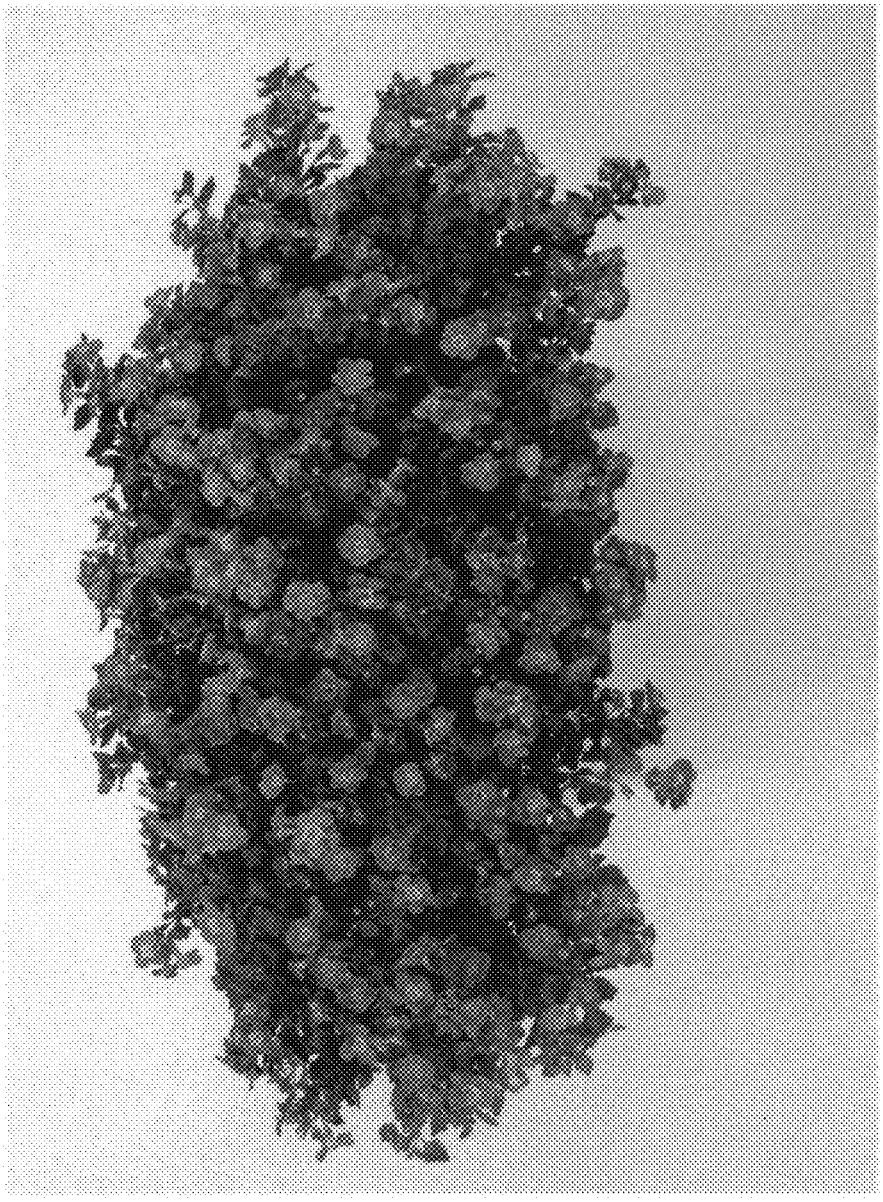

Latin name of the genus and species: *Sutera cordata.*
Variety denomination: 'DCOPGRAZUR'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The open pollination resulting in this new variety was made during October of 2011.

The seed parent is the unpatented, proprietary variety referred to as *Sutera* 'cv. 11-1972'. The pollen parent is unknown as it was an open pollination breeding program. The new variety was discovered in May of 2012 by the inventor in a group of seedlings resulting from the 2010 open pollination, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in May of 2012 and has shown that the unique features of this cultivar are stable and reproduced true to type in more than 20 successive generations.

SUMMARY OF THE INVENTION

The cultivar 'DCOPGRAZUR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCOPGRAZUR' These characteristics in combination distinguish 'DCOPGRAZUR' as a new and distinct *Sutera* cultivar:

1. Semi-trailing growth habit.
2. Extra-large, violet flowers with a purple center halo.
3. Moderately branched.
4. Early, abundant flowering.
5. Medium vigor.

Plants of the new cultivar 'DCOPGRAZUR' are similar to plants of the seed parent, *Sutera* 'cv. 11-1972' in most horticultural characteristics, however, plants of the new cultivar 'DCOPGRAZUR' differ in the following;

1. Plant habit of the new variety is mounded. The parent habit is semi-trailing.
2. The new variety has larger, darker flowers than the parent.
3. The new variety flowers more abundantly than the parent.

COMMERCIAL COMPARISON

Plants of the new cultivar 'DCOPGRAZUR' are comparable to the unpatented commercial variety *Sutera* 'DANCOP30'. The two *Sutera* varieties are similar in most horticultural characteristics; however, the new variety 'DCOPGRAZUR' differs in the following:

1. Comparison variety has large, blue flowers, whereas new variety has extra-large, violet flowers with a purple center halo.
2. Comparison variety is very well branched whereas new variety is less well branched.
3. Comparison and new varieties have a medium vigor.

Plants of the new cultivar 'DCOPGRAZUR' can also be comparable to the patented commercial variety 'DANCOP102', U.S. Plant Pat. No. 26,521. The two *Sutera* varieties are similar in most horticultural characteristics; however, the new variety 'DCOPGRAZUR' differs in the following:

1. Comparison variety has extra-large, white flowers whereas new variety has extra-large, violet flowers with a purple center halo.
2. Comparison variety has longer branches than new variety.

BRIEF DESCRIPTION OF THE PHOTOGRAPHS

The accompanying photograph in FIG. 1 illustrates in full color a typical plant of 'DCOPGRAZUR' grown in a greenhouse, in a 13 cm pot. Age of the plant photographed is approximately 3 months old from a rooted cutting.

Figure 2:
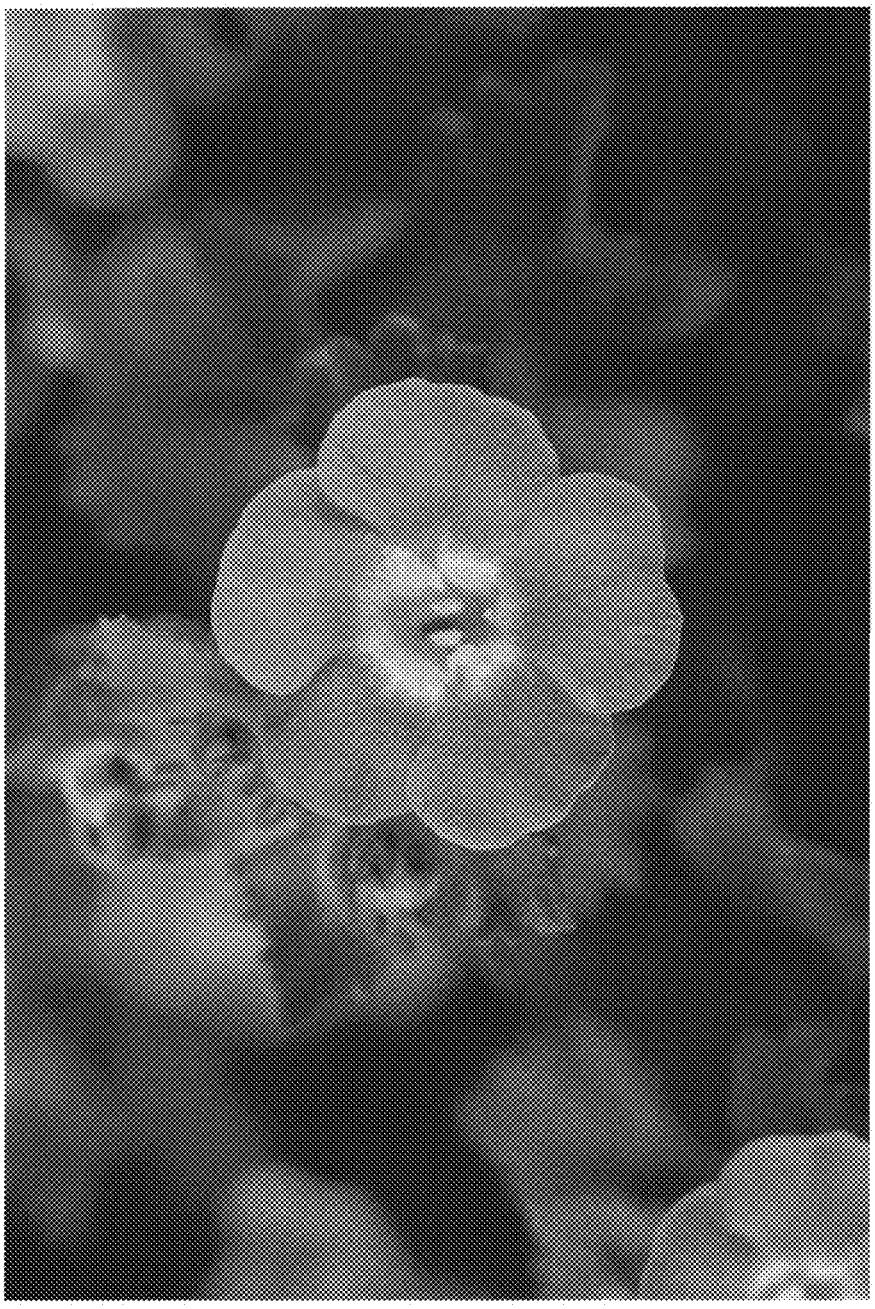

FIG. 2 illustrates a close up of a typical flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCOPGRAZUR' plants grown in the Winter to Spring in moderate climate in a greenhouse, in Moshav Mishmar Hashiva, Israel. The growing temperature ranged from 15° C. to 26° C. during the day and from 13° C. to 16° C. during the night. General light conditions are normal sunlight and numerical values represent averages of typical plant types.

Botanical classification: *Sutera cordata* 'DCOPGRAZUR'.

PROPAGATION

Type of propagation typically used: Terminal vegetative cuttings.

Time to initiate roots: 7 to 10 days at approximately 20° C.

Root description: Fine, fibrous roots. Light tan in color, not accurately measured with R.H.S. chart.

PLANT

Age of plant described: Approximately 3 months from rooted cutting.

Container size of the plant described: 13 cm.

Growth habit: Semi-trailing.

Height: Approximately 24 cm.

Plant spread: Approximately 50 cm.

Growth rate: Medium.

Branching characteristics:

*Length of primary lateral branches.*—About 25 cm.

*Diameter of lateral branches.*—About 0.2 cm.

*Quantity of primary lateral branches.*—About 8.

Characteristics of primary lateral branches:

*Form.*—Cylindrical.

*Diameter.*—About 0.3 cm.

*Color.*—RHS Yellow-Green 144 B.

*Texture.*—Velvety.

*Strength.*—Good.

Internode length: About 2 cm.

FOLIAGE

Leaf:

*Arrangement.*—Opposite, petiolate.

*Quantity.*—Approximately 60 per branch.

*Average length.*—2.5 cm.

*Average width.*—2.0 cm.

*Shape of blade.*—Ovate.

*Apex.*—Obtuse.

*Base.*—Acuminate.

*Margin.*—Serrate. Depth of serration: Medium.

*Texture of top surface.*—Velvety.

*Texture of bottom surface.*—Velvety.

*Pubescence.*—Slightly pubescent.

*Aspect.*—About 90° to the branch.

*Color.*—Young foliage upper side: RHS Green 137 B. Young foliage under side: RHS Green 137 C. Mature foliage upper side: RHS Green 137 A Mature foliage under side: RHS Green 137 B.

*Venation.*—Type: Pinnate. Venation color upper side: RHS Green 137 B. Venation color under side: RHS Green 137 C.

*Petiole.*—Length: About 0.5 cm. Diameter: About 0.2 cm. Color: RHS Green 137 C.

*Texture.*—Slightly velvety.

FLOWER

Natural flowering season: All year round.

Days to flowering from rooted cutting: About 45.

Inflorescence and flower type and habit: Axillary, solitary, salverform single flowers.

Rate of flower opening: 3 to 5 days from bud to fully opened flower.

Flower longevity on plant: About 7 days.

Persistent or self-cleaning: Persistent.

Bud:

*Shape.*—Spatulate.

*Length.*—About 1 cm.

*Diameter.*—About 0.5 cm.

*Color.*—RHS Violet N88 C.

Flower size:

*Diameter.*—About 2.5 cm.

*Length.*—About 1.2 cm.

*Corolla tube diameter.*—About 0.4 cm.

Corolla/petals:

*Arrangement.*—Symmetric.

*Lobe length.*—About 0.8 cm.

*Lobe width.*—About 1.2 cm.

*Quantity.*—5.

*Texture.*—Velvety.

*Lobe apex.*—Rounded.

*Lobe shape*.—Rounded.
*Margin*.—Entire.
*Aspect*.—About 90° to the tube.

Color:
*When opening*.—Upper surface: RHS Violet N88 B, center halo Purple N78 A. Thin inner halo near White N155 B. Visible Corolla throat near Yellow-Orange 15 A. Lower surface: RHS Violet N88 C.
*Fully opened*.—Upper surface: RHS Violet N87 B, center halo Purple N78 B. Inner halo near White N155 B. Visible Corolla throat near Yellow-Orange 15 A. Lower surface: RHS Violet N88 C.
*Visible inner corolla tube color*.—RHS Yellow-Orange 15 A.

Calyx/sepals:
*Quantity per flower*.—5.
*Shape*.—Linear.
*Length*.—About 0.8 cm.
*Width*.—About 0.1 cm.
*Apex*.—Acute.
*Base*.—Fused.
*Margin*.—Entire.
*Texture*.—Slightly velvety.
*Color*.—Upper Surface: RHS Green 137 C. Lower Surface: RHS Green 137 C.

Peduncle: None.

Pedicel:
*Length*.—Approximately 0.8 cm.
*Diameter*.—Approximately 0.1 cm.
*Color*.—Near RHS Green 137 D.
*Orientation*.—Slanted upward and outward.
*Pubescence*.—Slightly pubescent.

Fragrance: None.

REPRODUCTIVE ORGANS

Stamens:
*Number*.—4.
*Filament length*.—Approximately 1.2 cm.

Anthers:
*Shape*.—Cylindrical.
*Length*.—Approximately 0.2 cm.
*Color*.—RHS Yellow-Orange 15 B.
*Pollen*.—Color: RHS Yellow-Orange 15 A. Quantity: Sparse.

Pistil:
*Number*.—1.
*Length*.—About 1.1 cm.
*Style*.—Length: About 1.1 cm. Color: RHS Yellow Green-145 B.
*Stigma*.—Shape: Undulate. Color: RHS Yellow Green-146 C. Ovary Color: RHS Yellow-Green 146 C.

OTHER CHARACTERISTICS

Seeds and fruits: About 30 elliptic, small (1 mm long) brown seeds per one elliptic brown capsule. Seeds too small for accurate measurement with R.H.S. chart. Capsule color varies from tan to medium brown with age, near Grey-Brown 199A when just mature to 199D with age.

Disease/pest resistance: Neither resistance nor susceptibility to pathogens and pests common to *Sutera* have been observed.

Temperature tolerance: The new variety tolerates temperatures between 5 to 40° C.

What is claimed is:

1. A new and distinct cultivar of *Sutera* plant named 'DCOPGRAZUR' as herein illustrated and described.

* * * * *